United States Patent [19]

Pantukh et al.

[11] Patent Number: 5,364,974
[45] Date of Patent: Nov. 15, 1994

[54] PROCESS FOR THE PREPARATION OF 3,5-DI-TERT-BUTYL-4-HYDROXY METHOXYBENZYL ALCOHOL

[75] Inventors: Boris I. Pantukh; Igor J. Logutov; Nikolai V. Ljubimov; Grigory I. Rutman, all of Bashkortostan, Russian Federation

[73] Assignee: Sterlitamaxky Neftekhimichesky Zavod, Bashkortostan, Russian Federation

[21] Appl. No.: 171,354

[22] Filed: Dec. 21, 1993

[51] Int. Cl.$^5$ .............................. C07C 43/02
[52] U.S. Cl. ................................... 568/662
[58] Field of Search ......................... 568/662

[56] References Cited

U.S. PATENT DOCUMENTS

| | | | |
|---|---|---|---|
| 2,841,624 | 7/1958 | Norton et al. | 568/662 |
| 3,006,969 | 10/1961 | Koetitz | 568/662 |
| 4,754,077 | 6/1988 | Mina | 568/662 |
| 4,952,736 | 8/1990 | Iwahara | 568/662 |

FOREIGN PATENT DOCUMENTS 395351 1/1971 Russian Federation .

OTHER PUBLICATIONS

Koetitz, K. F. "Alkylated Phenols" Abstract Journal of Chemistry, 1963, Oct. 31, 1961.

*Primary Examiner*—Alan Siegel
*Attorney, Agent, or Firm*—Ladas & Parry

[57] ABSTRACT

Claimed is a process for the preparing 3,5-di-tert-butyl-4-hydroxy-methoxybenzyl alcohol which is an effective stabilizer of polymer materials and a starting compound in synthesis of high- effective polynuclear phenolic stabilizers.

It is an object of this invention to provide a simplification of the process and improve a quality of the target product.

This object is attained by using N,N,N',N'-tetra-methyl-methylene-bis-amine as a catalyst with the molar ratio of 2,6-DTBP to formaldehyde to methanol to bis-amine as of 1.0:1.0–1.5:10-15: 0.01–0.50 and conducting a process at 60°–100° C.

1 Claim, No Drawings

PROCESS FOR THE PREPARATION OF 3,5-DI-TERT-BUTYL-4-HYDROXY METHOXYBENZYL ALCOHOL

The present invention relates to processes for the preparing 3,5-di-tert-butyl-4-hydroxy-methoxybenzyl alcohol which is an effective stabilizer for polymer materials and a starting compound in the synthesis of high-effective polynuclear phenolic stabilizers.

U.S. Pat. No. 3,006,969 discloses a process for the preparation of 3,5-di-tert-butyl-4-hydroxybenzyl alcohol by condensation of 2,6-di-tert-butylphenol (2,6-DTBP) with formaldehyde and methanol in alkaline medium. A condensation provides the product having the ground substance of about 80 wt % and melting point (m.p.) of 92°–97° C. Recrystallization from methyl alcohol or petroleum ether afforded the product with m.p. of 101°–102° C. but low yield of not over 26%. A process is of preparative character, the final product contains more than 5 wt % of 4,4'-methylene-bis(2,6-di-tert-butylphenol)-(MB-1) having a negative effect on polymer color when using a compound as an antioxidant.

SU-A-395,351 discloses a process for the preparing 3,5-di-tert-butyl-4-hydroxybenzyl alcohol by reacting 2,6-DTEP with methanol and aqueous formaldehyde in the presence of buffer catalyst being a mixture of NaOH and $CH_3COONa$.

According to this process the reaction is carried out in four cycles at a pH in the range of 12.5–14.0 and at a temperature of 60° C. Once the each cycle had been over a suspension formed is cooled, a part of the target product is isolated by filtration and to the filtrate is further added 2,6-DTBP, formalin and methanol. The overall time of synthesis is about 4–6 hours. After reaching a pH value up to 7, the total yield of the target product (after four cycles) is about 85 wt % and the content of MB-1 compound is about 4 wt %.

The drawback to this process is a relatively low yield of the final product and instability of its make-up due to the presence of MB-1 compound. Moreover, the synthesis is time-consuming because of four-step process which is characterized in that the product on each subsequent cycle is inferior to that of the preceding cycle. This is supported by the m.p. values of the product obtained as compared with the reference data for 3,5-di-tert-butyl-4-hydroxy-methoxybenzyl alcohol.

| Cycle 1 | m.p. 98.6–99.0° C. |
|---|---|
| Cycle 2 | m.p. 97.4–98.6° C. |
| Cycle 3 | m.p. 96.2–97.0° C. |
| Cycle 4 | m.p. 69.0–96.7° C. |
| Reference data* | m.p. 99.5–101.0° C. |

*Handbook. Chemical Additives to Polymers. Moscow., Khimija Publishers, 1973, p. 60.

Thus, said prior art process produces quaternary product of non-uniform and unstable make-up which is inconsistent with the reference data for melting point. Furthermore, a realization of four-cycle synthesis abruptly increases the rate of formalin and methanol per mole 2,6-DTBP.

A multistage process determines a high duration of the reaction (4–6 hours) and a realization of complex technological procedures such as filtration, washing, discharge and isolation of the target product. The use of an alkali as a catalyst gives no way of making a profit from still bottoms of the solvent regeneration step.

Moreover, the large amounts of waste water produced by dilution of the reaction components such as the dead catalyst, methanol and formalin (which is effected to adjust their content to permissible values for disposal) further increase drawbacks to the prior art process.

It is an object of the present invention to provide a simplification of the process and produce the final product of stable and good quality.

This object as stated is attained by using N,N,N',N'-tetra-methylaminomethane (N,N,N',N'-tetra-methyl-methylene-bis-amine, bisamine) as a catalyst at the molar ratio of 2,6-DTBP to formaldehyde to methanol to bisamine as of 1.0:1.0–1.5:10–15: 0.01–0.50, with the process being conducted at a temperature of 60°–100° C.

According to the present invention a process for the preparation of 3,5-di-tert-butyl-4-hydroxy-methoxybenzyl alcohol as compared with the prior art is the one-step process and makes it possible to provide a high enough yield of the target product.

When carrying out a process the reaction rate proved to unexpectedly remain rather high throughout the synthesis which allowed a condensation step to conduct in a short time (2–4 hours), with the final pH value being close to 7.0 resulting in appreciable reducing an amount of the washing methanol. Very important result of such a process is a substantial simplification of the solvent regeneration step since a catalyst remains chemically fixed and fails to "spread" within the regeneration system.

According to the present invention the starting compounds must conform to the following requirements:

| 2,6-DTBP | m.p. 36.0–36.5° C.; purity is no less than 99 wt % |
|---|---|
| Methanol | Technical grade |
| Formaldehyde | 35–37% aqueous solution (formalin) |
| N,N,N',N'-tetra-methyl-methylene-bis-amine | Purity is less than 95 wt % |

The following Examples are intended to support the process as claimed.

EXAMPLE 1

2,6-DTBP (412 grams, 2 moles), methanol (832 grams, 26 moles), 35% formaldehyde solution (220 grams, 26 moles) and bis-amine (10.2 grams, 0.1 moles) were placed into a 2 L-digester. The digester was sealed, the stirred reaction mixture was heated to 90° C. and then kept at 90° C. for 2 hours followed by cooling to 15°–20° C.

A suspension formed was filtered off, the solids were washed with methanol (40 g) and dried. This afforded 434 grams of desired product as crystals (86.8% yield of the theoretical) with the final MB-1 content as of 2.1 wt % and melting point as of 99.5°–100.3° C.

Tests 2–5 listed in Table I illustrate a process for the preparation of 3,5-di-tert-butyl-4-hydroxy-methoxybenzyl alcohol within the limits of desired reaction conditions, Tests 6–11 apply to the reaction conditions different from that claimed in the present invention.

As can be seen from the data given in Table, the claimed molar ratio of the reagents makes it possible to produce the target product with the yield of 85.1–87.4 wt % and final content of MB-1 as an impurity of no more than 3 wt % without effecting any extra recrystallization step.

The use of a lesser concentration of catalyst (Test 6) reduces the rate of the main reaction which has effect on the yield and purity of the target product. When the bis-amine content is more than that used according to the present invention (Test 7) the yield of the product is comparable to Tests 1–5 however the final product calls for further recrystallization due to the increased content of MB-1 compound. The same occurs when excessive amount of formaldehyde is used (Test 8). Lowering a formaldehyde content to the value less than equimolar concentration of 2,6-DTBP (Test 9) causes the reaction to be abruptly inhibited and reduces the yield of the target product. Other reaction conditions being optimal, a rise in the temperature over 100° C. increases the MB-1 concentration (Test 10). The use of more of the methanol has no effect on a quality of the target product (Test 11) but reduces the yield and increases the volume of a solvent in the regeneration system.

Thus, the claimed process for the preparing 3,5-di-tert-butyl-4-hydroxy-methoxybenzyl alcohol provides a technological effectiveness of the process, high yield and stable quality of the target product which is of great importance when using it as a starting material in producing effective polynuclear phenolic stabilizers such as tris(3,5-di-tert-butyl-4-hydroxybenzyl)-mesitylene.

TABLE I

| Test No. 1 | Molar ratio of reagents | | | | Target product properties | | | |
|---|---|---|---|---|---|---|---|---|
| | 2,6-DTBP 2 | $CH_2O$ 3 | $CH_3OH$ 4 | Bisamine 5 | Reaction T, °C./hour 6 | Yield % 7 | MB-1 content, wt % 8 | t °C. 9 |
| 2. | 1.0 | 1.0 | 10 | 0.01 | 60/1.0 | 85.1 | 2.9 | 99.5–100.3 |
| 3. | 1.0 | 1.2 | 15 | 0.05 | 80/1.5 | 87.2 | 2.2 | 99.8–100.2 |
| 4. | 1.0 | 1.5 | 12 | 0.50 | 90/2.0 | 86.4 | 2.8 | 100.4–101 |
| 5. | 1.0 | 1.3 | 10 | 0.10 | 100/1.5 | 87.4 | 2.9 | 100.5–101.2 |
| 6. | 1.0 | 1.2 | 15 | 0.005 | 100/2 | 76.6 | 3.2 | 96.3–98.1 |
| 7. | 1.0 | 1.2 | 15 | 0.80 | 80/1.5 | 86.1 | 4.8 | 98.2–99.0 |
| 8. | 1.0 | 1.6 | 15 | 0.30 | 50/1.5 | 64.9 | 5.2 | 94.7–98.1 |
| 9. | 1.0 | 0.9 | 10 | 0.50 | 90/1.5 | 71.2 | 1.9 | 97.2–98.6 |
| 10. | 1.0 | 1.2 | 15 | 0.20 | 110/2 | 84.4 | 3.7 | 98.8–99.7 |
| 11. | 1.0 | 1.2 | 20 | 0.40 | 90/2 | 84.1 | 2.3 | 99.0–99.7 |

What is claimed is:

1. A process for the preparation of 3,5-di-tert-butyl-4-hydroxy-methoxybenzyl alcohol by reacting 2,6-tert-butylphenol with formaldehyde and methanol in the presence of a basic catalyst at elevated temperature characterized in that used as a catalyst is N,N,N', N'-tetra-methyl-di-aminomethane compound and the process is carried out at a temperature in the range of 60°–100° C. with the molar ratio of 2,6-di-tert-butylphenol to formaldehyde to methanol to catalyst of 1.0:1.0–1.5:10–15:0.01–0.50.

* * * * *